United States Patent
Shin et al.

(10) Patent No.: US 11,016,160 B2
(45) Date of Patent: May 25, 2021

(54) PARKINSON'S DISEASE DIAGNOSING APPARATUS AND METHOD

(71) Applicant: Heuron Co., Ltd., Incheon (KR)

(72) Inventors: Dong Hoon Shin, Incheon (KR); Hwan Heo, Incheon (KR); Eung Yeop Kim, Incheon (KR); Young Hee Sung, Gwacheon-si (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 16/652,315

(22) PCT Filed: Sep. 5, 2019

(86) PCT No.: PCT/KR2019/011462
§ 371 (c)(1),
(2) Date: Mar. 30, 2020

(87) PCT Pub. No.: WO2020/055039
PCT Pub. Date: Mar. 19, 2020

(65) Prior Publication Data
US 2020/0264253 A1    Aug. 20, 2020

(30) Foreign Application Priority Data

Sep. 10, 2018   (KR) .................. 10-2018-0107998

(51) Int. Cl.
*G01R 33/56* (2006.01)
*A61B 5/055* (2006.01)
(Continued)

(52) U.S. Cl.
CPC ........ *G01R 33/5608* (2013.01); *A61B 5/0042* (2013.01); *A61B 5/055* (2013.01);
(Continued)

(58) Field of Classification Search
CPC ................ G01R 33/50; G01R 33/5608; G01R 33/5616; G06T 11/008; G06T 2207/10088;
(Continued)

(56) References Cited

U.S. PATENT DOCUMENTS

2002/0115930 A1    8/2002   Hutchinson
2011/0286650 A1*  11/2011   Roy ..................... A61B 5/4088
                                                        382/131
(Continued)

FOREIGN PATENT DOCUMENTS

CN        108186133 A  *  6/2018
JP        2012-521244 A     9/2012
(Continued)

OTHER PUBLICATIONS

Cheng et al. "Radiomic Features of the Nigrosome-1 Region of the Substantia Nigra: Using Quantitative Susceptibility Mapping to Assist the Diagnosis of Idiopathic Parkinson's Disease." Frontiers in Aging Neuroscience: 11. Published Jul. 16, 2019.*
(Continued)

*Primary Examiner* — Amanda Lauritzen Moher
(74) *Attorney, Agent, or Firm* — Sughrue Mion, PLLC (57) ABSTRACT

Disclosed are Parkinson's disease diagnosing apparatus and method and a configuration which includes an image acquiring unit which acquires a multi-echo magnitude and a phase image from MRI obtained by capturing a brain of a patient, an image processing unit which post-processes only substantia nigra and a nigrosome-1 region proposed as an imaging biomarker of the Parkinson's disease from the acquired image to be observed; an image analyzing unit which classifies images including the nigrosome-1 region by analyzing the processed images and detects the nigrosome-1 region from the classified image, and a diagnosing unit
(Continued)

which determines whether the nigrosome-1 region is normal in the classified image to diagnose the Parkinson's disease is provided so that only the image which includes the nigrosome-1 region is classified in the MRI and the nigrosome-1 region is analyzed from the classified image to diagnose the Parkinson's disease.

3 Claims, 8 Drawing Sheets

(51) Int. Cl.
    *A61B 5/00*        (2006.01)
    *G01R 33/50*      (2006.01)
    *G06T 7/00*        (2017.01)
    *G06T 11/00*      (2006.01)
    *G16H 50/20*      (2018.01)
    *G06T 7/11*        (2017.01)

(52) U.S. Cl.
    CPC .......... *A61B 5/4082* (2013.01); *A61B 5/7264* (2013.01); *G01R 33/50* (2013.01); *G06T 7/0012* (2013.01); *G06T 7/11* (2017.01); *G06T 11/008* (2013.01); *G16H 50/20* (2018.01); *A61B 5/7267* (2013.01); *A61B 2576/026* (2013.01); *G06T 2207/10088* (2013.01); *G06T 2207/20081* (2013.01); *G06T 2207/30016* (2013.01)

(58) Field of Classification Search
    CPC . G06T 2207/20081; G06T 2207/20084; G06T 2207/30016; G06T 7/0012; G06T 7/11; G06T 2207/20016; G06T 3/40; G16H 50/20; G16H 30/20; G16H 10/40; G16H 30/40; G06N 3/04; G06N 3/08; G06K 2209/051; G06K 9/6267; G06K 9/3208; A61B 2576/026; A61B 5/00; A61B 5/0042; A61B 5/055; A61B 5/4082; A61B 5/7264; A61B 5/7267; A61B 4/082; A61B 5/7282

See application file for complete search history.

(56) References Cited

U.S. PATENT DOCUMENTS

2012/0321162 A1\* 12/2012 Liu .................... G01R 33/5616 382/131
2016/0252597 A1\* 9/2016 Liu .......................... A43B 3/00 324/309
2021/0007603 A1\* 1/2021 Huddleston ............ G16H 50/20

FOREIGN PATENT DOCUMENTS

| JP | 2015116319 | A | 6/2015 |
| JP | 2016131754 | A | 7/2016 |
| KR | 10-0674326 | B1 | 1/2007 |
| KR | 2014-0049137 | A | 4/2014 |
| KR | 10-2016-0012758 | A | 2/2016 |
| KR | 10-2016-0058812 | A | 5/2016 |
| KR | 10-1754291 | B1 | 7/2017 |

OTHER PUBLICATIONS

Schwarz et al. "The 'Swallow Tail' Appearance of the Healthy Nigrosome—A New Accurate Test of Parkinson's Disease: A Case-Control and Retrospective Cross-Sectional MRI Study at 3T." PLoS One. 2014; 9(4): e93814. Published online Apr. 7, 2014.\*
Xu et al. "Use of Magnetic Resonance Imaging and Artificial Intelligence in Studies of Diagnosis of Parkinson's Disease." ACS Chem. Neurosci. 2019, 10, 2658-2667. Published May 14, 2019.\*
Xiao et al. "Quantitative susceptibility mapping based hybrid feature extraction for diagnosis of Parkinson's disease." NeuroImage: Clinical. vol. 24, 2019. Published Nov. 5, 2019.\*
Mohsen et al. "Location Sensitive Deep Convolutional Neural Networks for Segmentation of White Matter Hyperintensities." Scientific Reports | 7: 5110. Published online Jul. 11, 2017.\*
Wroge et al. "Parkinson's Disease Diagnosis Using Machine Learning and Voice." 2018 IEEE Signal Processing in Medicine and Biology Symposium (SPMB), Philadelphia, PA, 2018, pp. 1-7.\*
Haller et al. "Differentiation between Parkinson disease and other forms of Parkinsonism using support vector machine analysis of susceptibility-weighted imaging (SWI): initial results." European Radiology vol. 23, 2013, pp. 12-19. Published online Jul. 15, 2012.\*
Heim et al. "Magnetic resonance imaging for the diagnosis of Parkinson's disease." J Neural Transm (2017) 124:915-964.\*
Huppertz et al. "Differentiation of neurodegenerative parkinsonian syndromes by volumetric magnetic resonance imaging analysis and support vector machine classification." Mov Disord Oct. 2016;31(10):1506-1517.\*
Huang et al. "Susceptibility-weighted imaging in detecting brain iron accumulation of Parkinson's disease" (Chinese language). Zhonghua Yi Xue Za Zhi Nov. 23, 2010;90(43):3054-8.\*
English translation of Huang et al. "Susceptibility-weighted imaging in detecting brain iron accumulation of Parkinson's disease" (Chinese language original). Zhonghua Yi Xue Za Zhi Nov. 23, 2010;90(43):3054-8. Provided by USPTO STIC machine translation services Dec. 17, 2020.\*
Haacke et al. "Susceptibility Weighted Imaging (SWI)." Magnetic Resonance in Medicine 52:612-618 (2004).\*
Salvatore et al. "Machine learning on brain MRI data for differential diagnosis of Parkinson's disease and Progressive Supranuclear Palsy." Journal of Neuroscience Methods 222 (2014) 230-237.\*
Cheng et al. "Imaging of the Nigrosome 1 in the Substantia Nigra Using Susceptibility Weighted Imaging and Quantitative Susceptibility Mapping: An Application to Parkinson's Disease." NeuroImage: Clinical 25 (2020; available online Nov. 20, 2019).\*
Notice of Preliminary Rejection issued in the Korean Patent Office dated Feb. 25, 2020 in corresponding Korean Application No. 10-2018-0107998.
Notice of Preliminary Rejection issued in the Korean Patent Office dated May 8, 2020 in corresponding Korean Application No. 10-2018-0107998.
Notice of Allowance issued in the Korean Patent Office dated Jul. 1, 2020 in corresponding Korean Application No. 10-2018-0107998.
Sung-Min Gho, et al., "Susceptibility Map-Weighted Imaging (SMWI) for Neuroimaging", Magnetic Resonance in Medicine, 2014, pp. 337-346, vol. 72.
Yoonho Nam, et al., "Imaging of Nigrosome 1 in Substantia Nigra at 3T Using Multiecho Susceptibility Map-Weighted Imaging (SMWI)", J. Magn. Reson. Imaging 2017; pp. 528-536, vol. 46.
Christian Langkammer, et al., "Quantitative susceptibility mapping (QSM) as a means to measure brain iron? A post mortem validation study", Neuroimage, Sep. 2012, pp. 1593-1599, vol. 63.(3-2).
International Search Report for PCT/KR2019/011462 dated Jan. 7, 2020 [PCT/ISA/210].
Communication dated Nov. 6, 2020 , from the China National Intellectual Property Administration in Application No. 201980005028.5.
Communication dated Oct. 14, 2020 , from the European Patent Office in European Application No. 19859966.4.
Communication dated Dec. 2, 2020 , from the Japanese Patent Office in Application No. 2020-519106.
P. Gao et al. "Visualization of nigrosomes-1 in 3T MR susceptibility weighted imaging and its absence in diagnosing Parkinson's disease", European Review for Medical and Pharmacological Sciences, vol. 19, 2015, pp. 4603-4609 (7 Pages Total).
K. Lee et al., "Investigation of the Healthy Nigrosome-1 for the Diagnosis of Parkinson's Disease using Multiple Susceptibility based MRI Techniques", Proc. Intl. Soc. Mag. Reson. Med, vol. 24., 2016, No. 1249 (2 Pages Total).

\* cited by examiner

PARKINSON'S DISEASE DIAGNOSING APPARATUS AND METHOD

CROSS REFERENCE TO RELATED APPLICATIONS

This application is a National Stage of International Application No. PCT/KR2019/011462 filed Sep. 5, 2019, claiming priority based on Korean Patent Application No. 10-2018-0107998 filed Sep. 10, 2018.

TECHNICAL FIELD

The present invention relates to a Parkinson's disease diagnosing apparatus and method, and more particularly, to a Parkinson's disease diagnosing apparatus and method which diagnose the Parkinson's disease by analyzing magnetic resonance imaging (hereinafter, abbreviated as 'MRI').

BACKGROUND ART

The neurodegenerative disorder refers to a disease which causes an abnormal brain function as nerve cells die due to some reasons.

Representative neurodegenerative disorders usually include Alzheimer's disease, Parkinson's disease, rarely, Lou Gehrig's disease, and the like.

Among the neurodegenerative disorders, the Parkinson's disease is a representative neurodegenerative disorder by which neural cells are destroyed and is accompanied by depression and anxiety together with symptoms such as rigidity, hand and foot tremors, and difficulty in walking so that the quality of life is greatly degraded.

The neurodegenerative disorder is diagnosed by a non-invasive method of diagnosing without contact with mucosa, skin break, and internal body cavity beyond a natural or artificial body orifice.

For example, in the following Patent Documents 1 and 2, a technology of diagnosing the neurodegenerative disorder according to the related art is disclosed.

Until now, [18F]FP-CIT Positron emission tomography (PET) using isotopes has been used as the most objective method for a diagnosis of Parkinson's disease and a differential diagnosis of drug-induced Parkinsonism.

However, [18F]FP-CIT PET is a very expensive test method and has a risk of radiation exposure.

Therefore, it is requested to develop a technology of diagnosing the Parkinson's disease by observing a nigrosome-1 region using the MRI.

RELATED ART DOCUMENT (Patent Document 1) Korean Registered Patent No. 10-1754291 (published on Jul. 6, 2017)
(Patent Document 2) Korean Unexamined Patent Application Publication No. 10-2016-0058812 (published on May 25, 2016)
(Non-Patent Document 1) Sung-Min Gho, et al., "Susceptibility Map-Weighted Imaging (SMWI) for Neuroimaging", Magnetic Resonance in Medicine 72:337-346(2014)
(Non-Patent Document 2) Yoonho Nam, et al., "Imaging of Nigrosome 1 in Substantia Nigra at 3 T Using Multiecho Susceptibility Map-Weighted Imaging (SMWI)", J. MAGN. RESON. IMAGING 2017; 46:528-536
(Non-Patent Document 3) Christian Langkammer, et al., "Quantitative susceptibility mapping (QSM) as a means to measure brain iron? A post mortem validation study", Neuroimage. 2012 September; 62(3):1593-9. doi: 10.1016/j.neuroimage.2012.05.049. Epub 2012 May 24.

DISCLOSURE

Technical Problem

An object of the present invention is to solve the problems as described above and to provide a Parkinson's disease diagnosing apparatus and method which diagnose the Parkinson's disease by analyzing the MRI.

Another object of the present invention is to provide a Parkinson's disease diagnosing apparatus and method which diagnose the Parkinson's disease by analyzing a nigrosome-1 region proposed as an imaging biomarker for the Parkinson's disease.

Technical Solution

In order to achieve the objects as described above, the Parkinson's disease diagnosing apparatus according to the present invention includes: an image acquiring unit which acquires a multi-echo magnitude and a phase image from MRI obtained by capturing a brain of a patient, an image processing unit which post-processes only substantia nigra and nigrosome-1 region proposed as an imaging biomarker of the Parkinson's disease from the acquired image to be observed; an image analyzing unit which classifies images including the nigrosome-1 region by analyzing the processed images and detects the nigrosome-1 region from the classified image, and a diagnosing unit which determines whether the nigrosome-1 region is normal from the classified image to diagnose the Parkinson's disease.

Further, in order to achieve the objects as described above, the Parkinson's disease diagnosing method according to the present invention generates a susceptibility map weighted imaging image including a nigrosome-1 region proposed as an imaging biomarker of the Parkinson's disease by applying a quantitative susceptibility mapping algorithm to an MRI captured by MRI equipment and analyzes the nigrosome-1 region from the generated image to diagnose the Parkinson's disease.

Advantageous Effects

As described above, according to the Parkinson's disease diagnosing apparatus and method of the present invention, only images including the nigrosome-1 region are classified from the MRI and the nigrosome-1 region is analyzed from the classified image to diagnose the Parkinson's disease.

Further, according to the present invention, a visibility of the nigrosome-1 region is improved by applying a susceptibility map weighted imaging protocol and a quantitative susceptibility mapping algorithm and the Parkinson's disease is diagnosed using an image with a visualized substantia nigra structure so that the Parkinson's disease can be more precisely diagnosed using the MRI device commonly supplied and the accuracy of the diagnosis result can be improved.

BEST MODE

Hereinafter, a Parkinson's disease diagnosing apparatus and method according to an exemplary embodiment of the present invention will be described in detail with reference to the accompanying drawings.

First, referring to FIG. 1, a criterion of diagnosing the Parkinson's disease by observing a nigrosome-1 region in a substantia nigra will be described.

Figure 1:
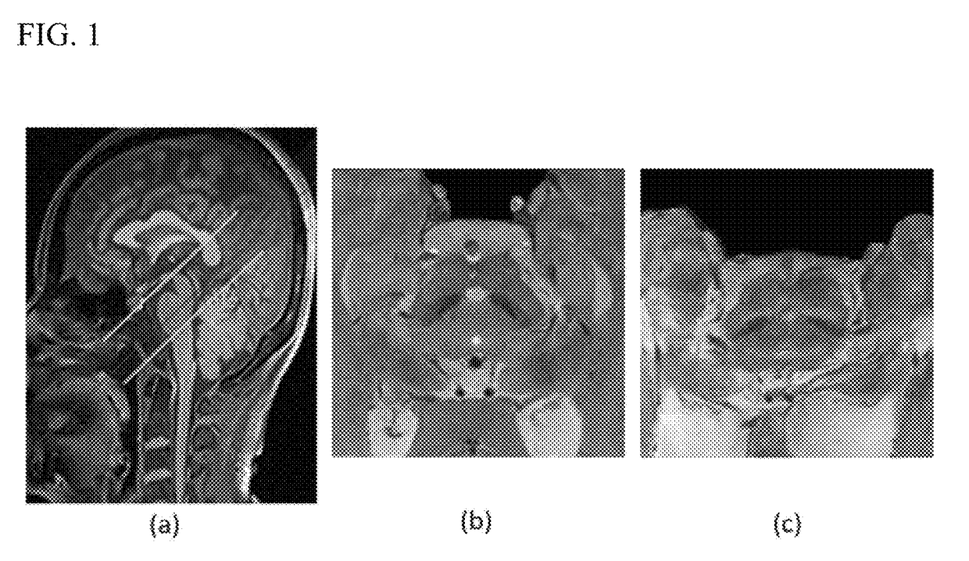
FIG. 1 is a view illustrating an MRI including a substantia nigra and a nigrosome-1 region.

FIG. 1 is a view illustrating an MRI including a substantia nigra and a nigrosome-1 region.

FIG. 1A illustrates an imaging slab, FIG. 1B illustrates an image of a substantia nigra and a nigrosome-1 region of normal people, and FIG. 1C illustrates an image of a substantia nigra and a nigrosome-1 region of a Parkinson's disease patient.

The nigrosome-1 region in the substantia nigra of the normal people is illustrated to be black as illustrated in FIG. 1B and the nigrosome-1 region of a patient with the Parkinson's disease is illustrated to be relatively grayish as illustrated in FIG. 1C.

Accordingly, according to the present invention, the Parkinson's disease may be diagnosed by observing a shadow of the nigrosome-1 region proposed as an imaging biomarker for the Parkinson's disease in the MRI.

For example, according to the present invention, the visibility of the nigrosome-1 region is improved by applying a susceptibility map weighted imaging (hereinafter, abbreviated as 'SMWI') protocol and a quantitative susceptibility mapping (hereinafter, abbreviated as 'QSM') algorithm therein to analyze whether the nigrosome-1 region is normal to diagnose the Parkinson's disease.

Substantia nigra pars compacta is a midbrain structure including a dense population of dopaminergic neurons. These neurons progressively disappear by the idiopathic Parkinson's disease (IPD) to cause disability. This region shows that the iron levels are increased in the IPD patient as compared to a healthy control group.

Recently, as a result of visualizing a small part of the substantia nigra pars compacta known as the nigrosome-1 in a high resolution susceptibility contrast image of a healthy subject, the contrast of the nigrosome-1 and neighboring substantia nigra regions therearound is caused by the difference in iron levels so that the susceptibility difference of two parts is significantly reduced in the IPD patient.

The reduction in the susceptibility of two parts as described above has been utilized as an imaging biomarker of the IPD.

Therefore, the nigrosome-1 structure was successfully described in 7 T MRI using high resolution (for example, 0.3 mm plane resolution) T2-weighted imaging or susceptibility weighted imaging (SWI).

However, a structure with a significantly reduced contrast is observed from a 3D high resolution T2-weighted imaging due to a limited spatial resolution and signal/contrast to noise ratio (SNR/CNR) in a low magnetic field intensity such as 3 T MRI.

This limitation has hindered the reliability and the applicability of the nigrosome-1 imaging in the 3 T MRI, despite several successful studies which prove the usefulness of the approach.

Recently, in order to solve the above-described problem, new methods for providing an improved magnetic susceptibility contrast have been proposed.

One of the methods is to couple multi-echo gradient recall echo (hereinafter, referred to as 'multi-echo GRE') magnitude images, instead of using a single echo image to improve the SNR, which has a relatively high accuracy in diagnosis of IPD in 3 T MRI.

An alternative of the magnitude image may generate artifacts due to blooming of susceptibility weighted imaging (SWI) which uses phase information as a weight mask to increase the susceptibility contrast or the phase imaging.

Another approach related to the susceptibility contrast is a GRE phase (or frequency) image and quantitative susceptibility mapping (QSM) and both are highly susceptible to the susceptibility and have been widely applied in recent years.

Further, a new method which uses a susceptibility weighting mask derived from the QSM for the magnitude image has been proposed.

This approach is similar to the SWI, but solves the blooming artifacts of the SWI and potentially improves the visualization of changes in susceptibility.

The QSM mask weighted imaging has proven to be useful for visualizing the nigrosome-1 structure.

In Non-Patent Document 1, a SMWI technique for neuroimaging is disclosed and in Non-Patent Document 2, an imaging technique of nigrosome-1 in substantia nigra using multi-echo SMWI in 3 T MRI is disclosed. Further, in Non-Patent Document 3, a QSM technique as a means to measure brain iron is disclosed.

Therefore, according to the present invention, the Parkinson's disease is diagnosed based on the change in the nigrosome-1 region due to the Parkinson's disease in accordance with the correlation of a brain iron level and the susceptibility.

Figure 2:
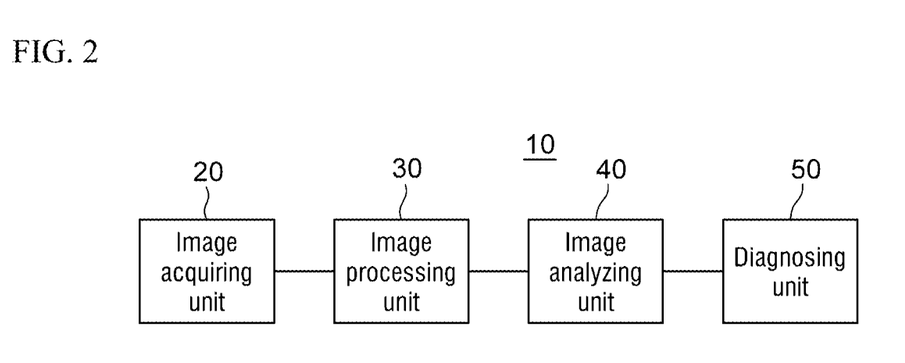
FIG. 2 is a block diagram of a Parkinson's disease diagnosing apparatus according to an exemplary embodiment of the present invention.

FIG. 2 is a block diagram of a Parkinson's disease diagnosing apparatus according to an exemplary embodiment of the present invention.

As illustrated in FIG. 2, a Parkinson's disease diagnosing apparatus 10 according to an exemplary embodiment of the present invention includes an image acquiring unit 20 which acquires a multi-echo magnitude and a phase image from an MRI obtained by capturing a brain of a patient, an image processing unit 30 which post-processes only substantia nigra and a nigrosome-1 region proposed as imaging biomarkers of the Parkinson's disease from the acquired image to be observed, an image analyzing unit 40 which analyzes the processed image to classify an image which includes the nigrosome-1 region and detects the nigrosome-1 region from the classified image, and a diagnosing unit 50 which determines whether the nigrosome-1 region is normal in the classified image to diagnose the Parkinson's disease.

A configuration of the image acquiring unit and the image processing unit will be described in detail with reference to FIG. 3.

Figure 3:
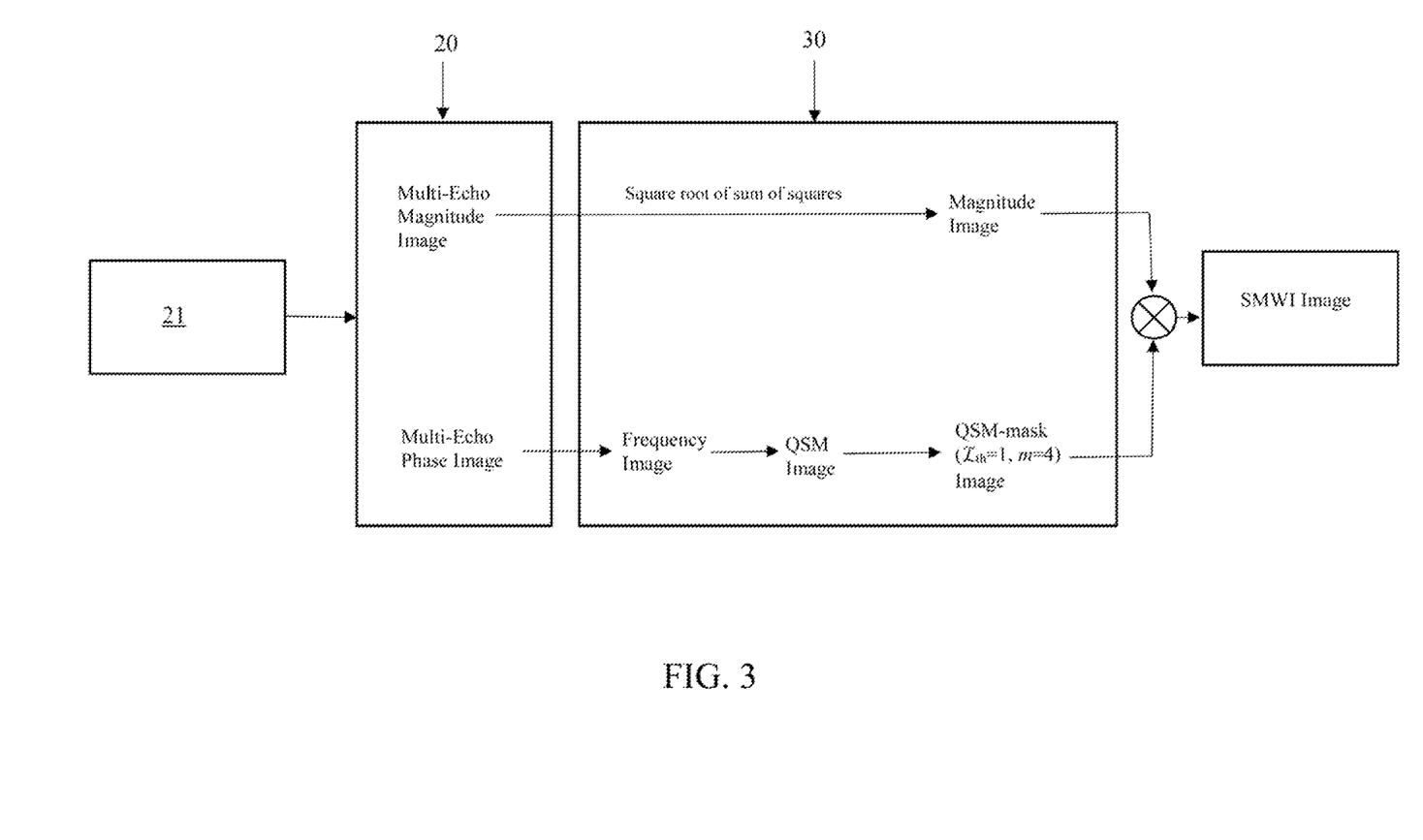
FIG. 3 is a view for explaining operations of an image acquiring unit and an image processing unit.

FIG. 3 is a view for explaining operations of an image acquiring unit and an image processing unit. In FIG. 3, a process of generating an SMWI image for the nigrosome-1 structure from a multi-echo composite GRE image is illustrated.

The image acquiring unit 20 is communicatively connected to MRI equipment 21 or a database (not illustrated in the drawing) which stores and controls MRI captured by the MRI equipment 21, as illustrated in FIG. 3, to acquire an MRI of a patient to diagnose the Parkinson's disease.

The image processing unit 30, as illustrated in FIG. 3, generates an SMWI image from a multi-echo GRE composite image in which a multi-echo magnitude image and a multi-echo phase image are composed, using the QSM algorithm, to visualize the nigrosome-1 structure.

For example, the image processing unit 30 generates a magnitude image which is channel-coupled by a square root of a sum of squares of the multi-channel magnitude image from the multi-channel composite image and the phase image is coupled as a complex average after correcting a global phase offset of individual channels (first step).

Further, the image processing unit 30 combines a single image by a square root of a sum of a square of six echo magnitude images (second step).

The image processing unit 30 calculates a phase image of different TE using a Laplacian unwrapping algorithm and calculates a frequency w combined in each voxel (third step).

The image processing unit 30 removes a background region from a frequency image using harmonic background phase removal using a Laplacian operator method (fourth step).

Here, the QSM may be reconstructed using an improved sparse linear equation and a least-square (iLSQR) method.

For example, in the constructed parameter of iLSQR, a tolerance is 0.01 (Tolerance=0.01), a threshold value D2 for incomplete k-region mask, thres is 0.1 ($D_{2,thres}$=0.1).

Next, the image processing unit 30 further processes a result QSM to generate a QSM mask ($S_{mask}$) for a susceptibility contrast weight (fifth step).

The mask may be generated using Equation 1.

$$S_{mask}(X) = \begin{cases} 0, & X_{th} < X \\ (X_{th} - X)/X_{th}, & 0 < X < Xth \\ 1, & \text{otherwise} \end{cases} \quad \text{[Equation 1]}$$

Here, X is a quantitative susceptibility value (ppm unit) calculated in the fourth step and $X_{th}$ is a paramagnetic threshold value. The threshold value may be determined using nigrosome-1 imaging data for an optimal CNR later.

Finally, the image processing unit 30 may generate an SMWI image by multiplying a multi-echo combined magnitude image and the QSM mask using the following Equation 2.

$$\text{SMWI} = (S_{mask})^m \times \text{mag} \quad \text{[Equation 2]}$$

Here, m is a number of multiplications for susceptibility weight and mag is a multi-echo magnitude combined image of the second step.

Next, an operation of the image analyzing unit will be described in detail with reference to FIGS. 4 and 5.

Figure 4:
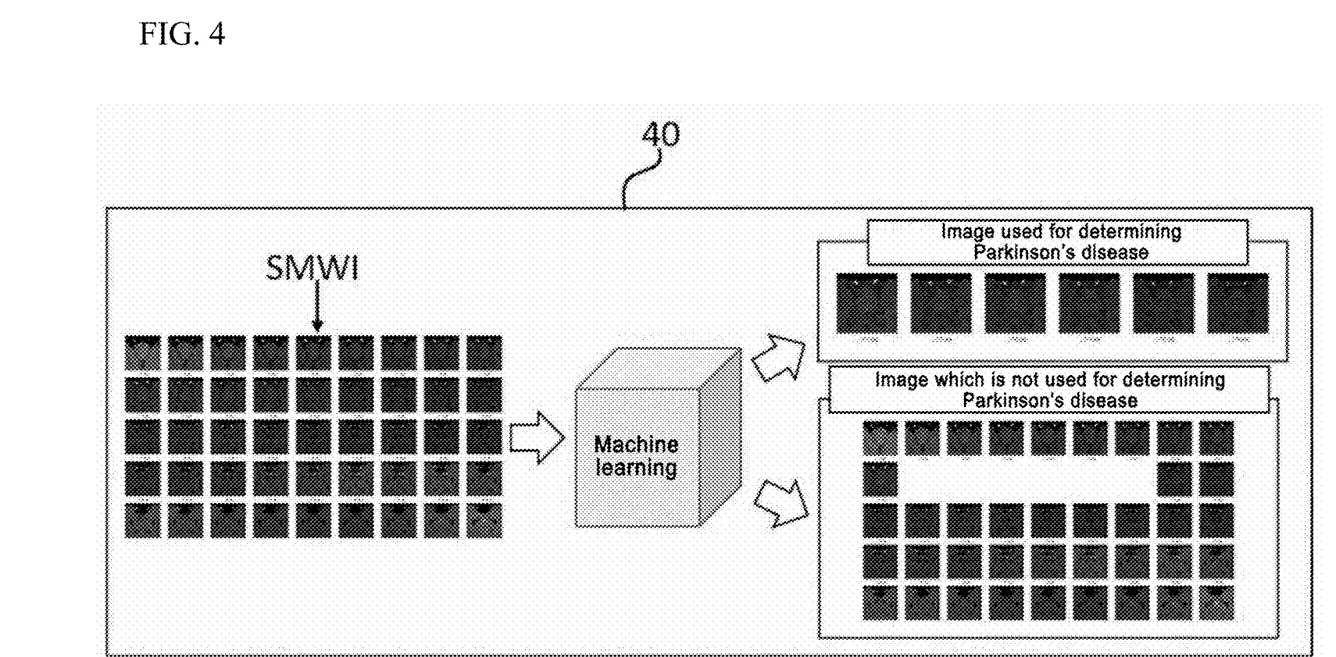
FIGS. 4 and 5 are views for explaining an operation of an image analyzing unit.
Figure 5:
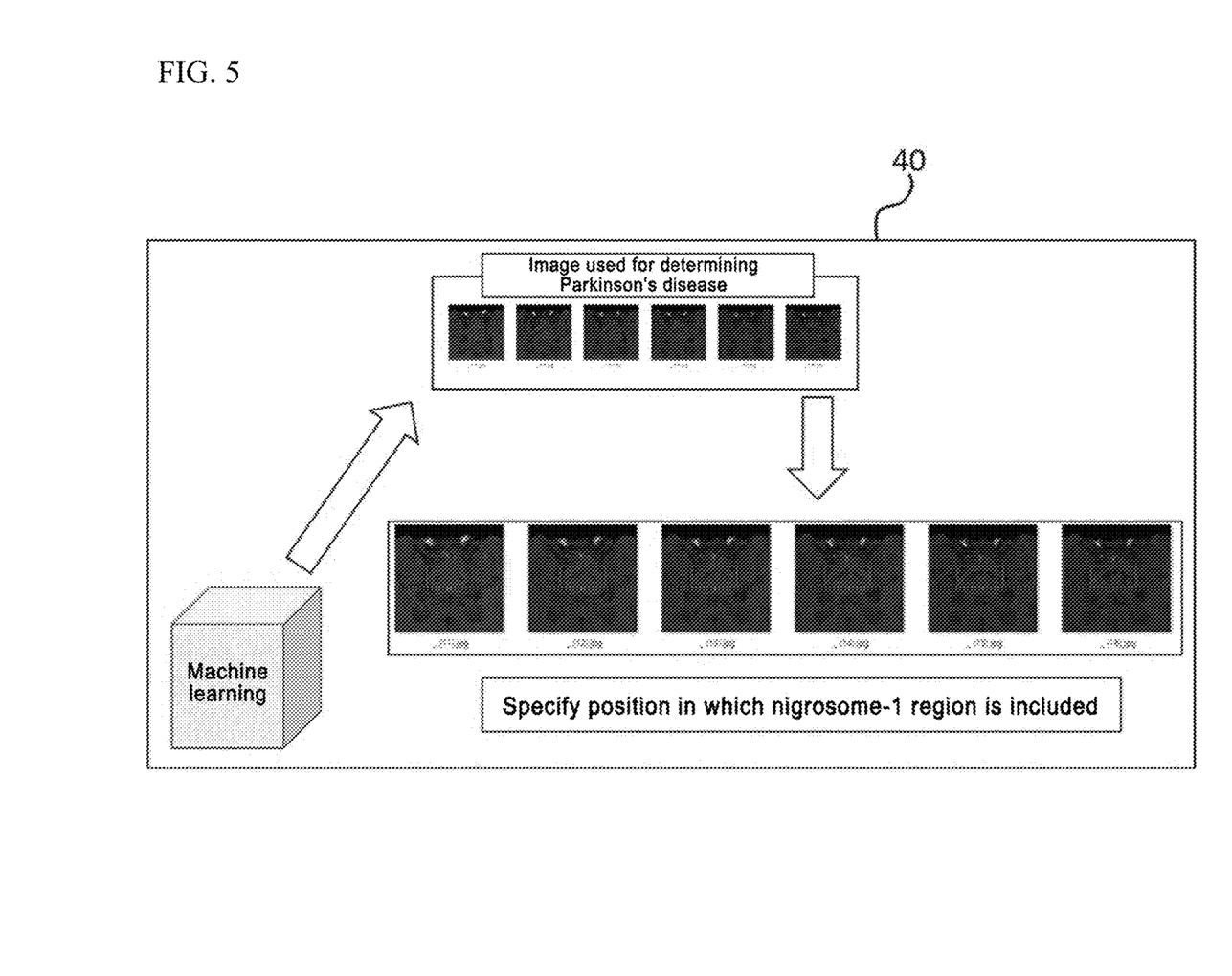

FIGS. 4 and 5 are views for explaining an operation of an image analyzing unit. FIG. 4 illustrates a process of classifying images including a nigrosome-1 region and FIG. 5 illustrates a process of detecting the nigrosome-1 region from the classified images.

As illustrated in FIG. 4, a plurality of SMWI images may be acquired by the post-processing process of the image processing unit 30.

Generally, the MRI captured for diagnosis of the Parkinson's disease is approximately 40 to 70 sheets for one patient and among them, approximately 3 to 6 sheets include the nigrosome-1 region used for diagnosis of the Parkinson's disease.

The image analyzing unit 40 analyzes the image which includes the nigrosome-1 region from the entire MRI through the machine learning to classify an image which includes the nigrosome-1 region and an image which does not include the nigrosome-1 region, as illustrated in FIG. 4.

For example, the image analyzing unit 40 classifies a region including the nigrosome-1 region using a region-convolutional neural network (hereinafter, abbreviated as 'RCNN') among methods using a deep learning neural network of the machine learning.

That is, the image analyzing unit 40 detects a feature map from an acquired image using a convolutional neural network (hereinafter, abbreviated as 'CNN'), selects approximately 2000 regions of interest (RoI) in the feature map detected using a region proposal network (hereinafter, abbreviated as 'RPN'), classifies each region of interest by performing CNN using a support vector machine (SVM) configured by a neural network to enhance the accuracy of the position of the region of interest to be input to the CNN after resizing the selected regions of interest to have the same size, and then processes the classified result with a classification loss and a bounding-box regression loss to be finally minimized only to an image including the nigrosome-1 region.

The image analyzing unit 40 specifies a position where the nigrosome-1 region is included, from each image including the nigrosome-1 region classified by the machine learning and detects the specified nigrosome-1 region, as illustrated in FIG. 5.

Next, an operation of the diagnosing unit will be described with reference to FIGS. 6 and 7.

Figure 6:
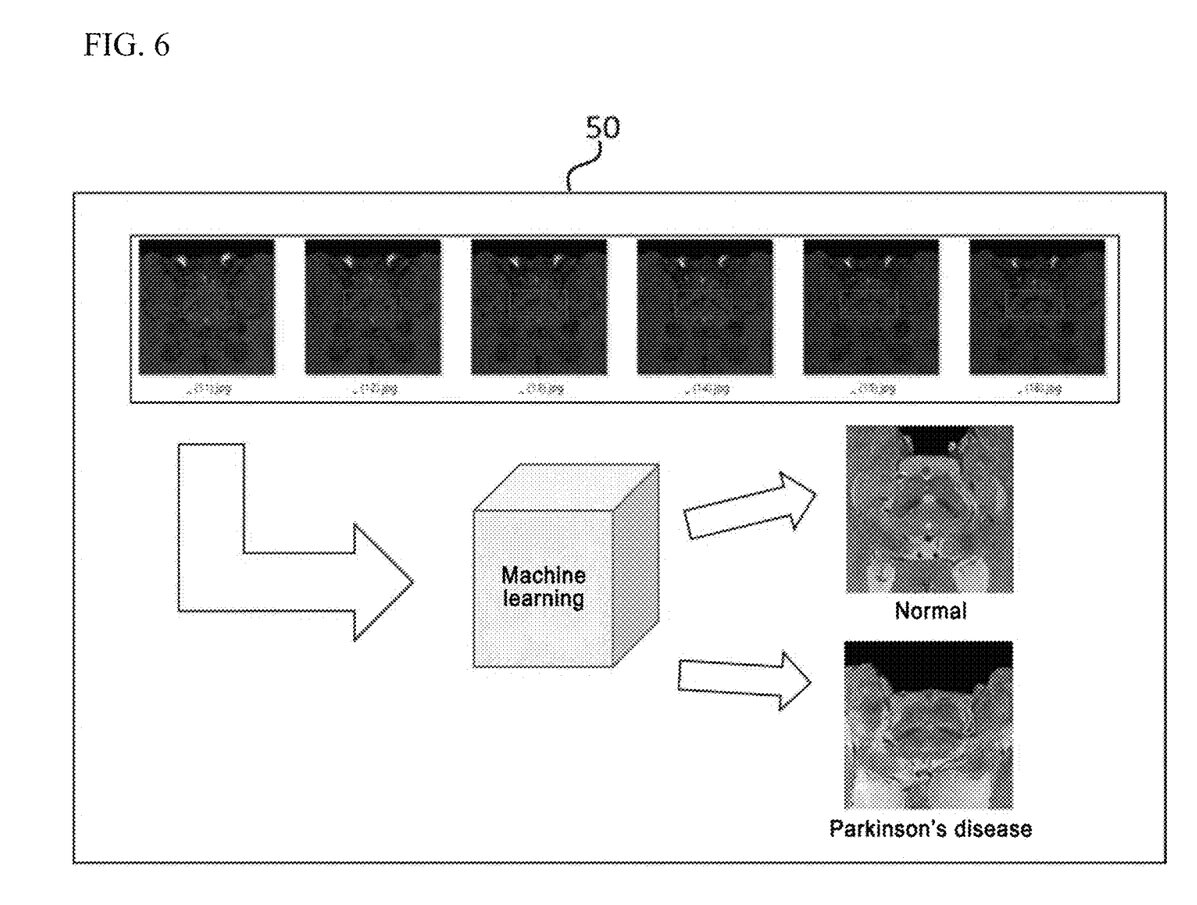
FIG. 6 is a view for explaining an operation of a diagnosing unit.
Figure 7:
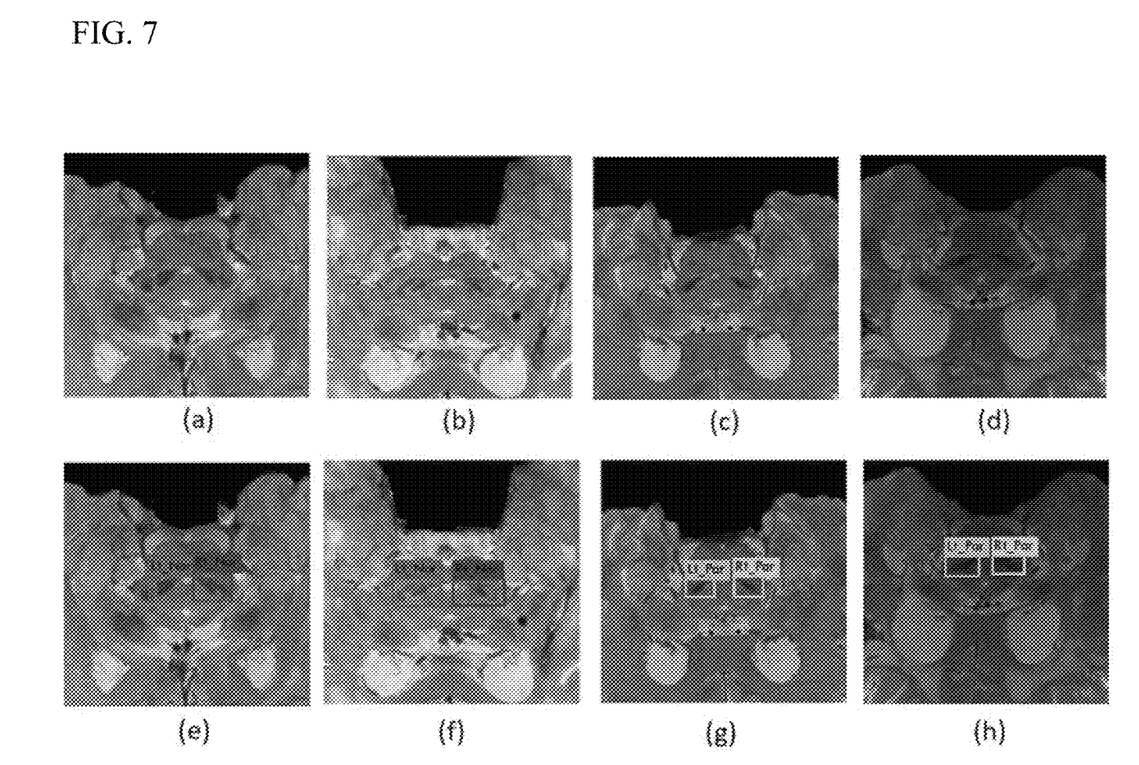
FIG. 7 is a view illustrating a state in which a diagnosis result is applied to an input image.

FIG. 6 is a view for explaining an operation of a diagnosing unit and FIG. 7 is a view illustrating a state in which a diagnosis result is applied to an input image.

The diagnosing unit 50 analyzes whether the nigrosome-1 region detected by the image analyzing unit 40 is normal through the machine learning to diagnose the Parkinson's disease, as illustrated in FIG. 6.

For example, a diagnosis result may be applied as illustrated in FIGS. 7E to 7H in accordance with a result of diagnosing whether it is a Parkinson's disease from the input image of FIGS. 7A to 7D.

Next, a Parkinson's disease diagnosing method according to an exemplary embodiment of the present invention will be described in detail with reference to FIG. 8.

Figure 8:
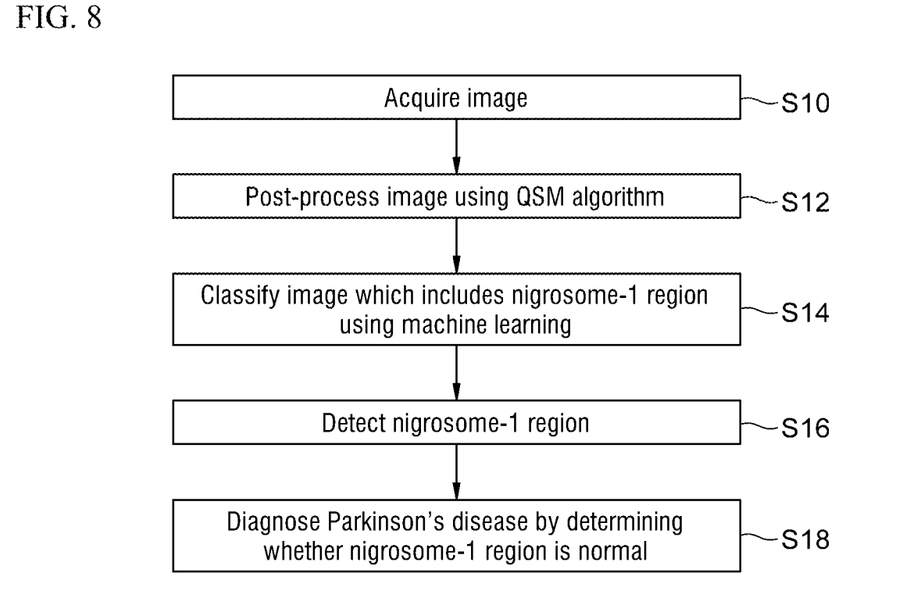
FIG. 8 is a flowchart for explaining a Parkinson's disease diagnosing method according to an exemplary embodiment of the present invention step by step.

FIG. 8 is a flowchart for explaining a Parkinson's disease diagnosing method according to an exemplary embodiment of the present invention step by step.

In step S10 of FIG. 8, the image acquiring unit 20 acquires a plurality of MRI of a patient to diagnose the Parkinson's disease through the communication with the MRI equipment 21 or the database.

Here, the image acquiring unit 20 may acquire a multi-echo GRE composite image in which a multi-echo magnitude image and a multi-echo phase image are composed from 3 T MRI.

In step S12, the image processing unit 30 generates an SMWI image by post-processing a multi-echo GRE composite image in which a multi-echo magnitude image and a multi-echo phase image are composed, using the QSM algorithm, to visualize the nigrosome-1 structure.

In step S41, the image analyzing unit 40 analyzes the image including the nigrosome-1 region from the entire MRI through the machine learning to classify an image which includes the nigrosome-1 region and an image which does not include the nigrosome-1 region.

Further, the image analyzing unit 40 specifies a position where the nigrosome-1 region is included, from each image which includes the nigrosome-1 region classified by the machine learning and detects the specified nigrosome-1 region (S16).

Finally, the diagnosing unit 50 determines whether the nigrosome-1 region detected from each image classified as an image which includes the nigrosome-1 region in the image analyzing unit 40 is normal to diagnose the Parkinson's disease.

Based on the above-described processes, the present invention may classify only images including the nigrosome-1 region from the MRI and analyze the nigrosome-1 region from the classified image to diagnose the Parkinson's disease.

As described above, even though the invention made by the inventor has been described in detail with exemplary embodiments, it is apparent that the present invention is not limited to the exemplary embodiment but various modifications and changes may be made without departing from the spirit of the present invention.

INDUSTRIAL APPLICABILITY

The present invention is applied to the Parkinson's disease diagnosing apparatus and method which diagnose the Parkinson's disease by classifying only an image including a nigrosome-1 region in the MRI and analyzing the nigrosome-1 region from the classified image.

The invention claimed is:

1. An apparatus for detecting Parkinson's disease, comprising:
   a memory comprising one or more instruction; and
   a processor configured to execute the one or more instruction to:
   acquire a plurality of multi-echo magnitude and phase images from produced by magnetic resonance imaging (MRI), the plurality of multi-echo magnitude and phase images being obtained by scanning a brain of a patient;
   post-process the plurality of acquired images to produce a plurality of processed images by:
     removing portions of the plurality of acquired images other than a substantia nigra and a nigrosome-1 region which are imaging biomarkers of Parkinson's disease;
     generating a plurality of frequency images based on the plurality of acquired phase images;
     generating a plurality of processed frequency images by removing a background phase from the plurality of frequency images using a Laplacian operator; and
     applying a quantitative susceptibility map mask to the plurality of processed frequency images based on a quantitative susceptibility mapping algorithm for visualizing the nigrosome-1 region;
   analyze the plurality of processed images to classify each of the plurality of processed image based on whether an image includes the nigrosome-1 region;
   detect the nigrosome-1 region in the images classified as including the nigrosome-1 region; and
   determine whether the nigrosome-1 region is normal in each of the images classified as including the nigrosome-1 region, according to a correlation between concentration of iron in the patient's brain and susceptibility to Parkinson's disease, based on an analysis of the nigrosome-1 region preformed using machine learning.

2. An apparatus for detecting Parkinson's disease according to claim 1, wherein the processor is further configured to post process the plurality of acquired images to produce a plurality of processed images by generating a susceptibility map weighted imaging image by applying the quantitative susceptibility map mask to the plurality of multi-echo magnitude and phase images.

3. An apparatus for detecting Parkinson's disease according to claim 2, wherein the quantitative susceptibility map mask is generated for a susceptibility contrast weight.

* * * * *